US010865419B2

United States Patent
Daniell (10) Patent No.: US 10,865,419 B2
(45) Date of Patent: Dec. 15, 2020

(54) ORALLY ADMINISTERED PLASTID EXPRESSED CHOLERA TOXIN B SUBUNIT-EXENDIN 4 AS TREATMENT FOR TYPE 2 DIABETES

(71) Applicant: UNIVERSITY OF CENTRAL FLORIDA RESEARCH FOUNDATION, INC., Orlando, FL (US)

(72) Inventor: Henry Daniell, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 53 days.

(21) Appl. No.: 14/353,980

(22) PCT Filed: Oct. 24, 2012

(86) PCT No.: PCT/US2012/061598
§ 371 (c)(1),
(2) Date: Apr. 24, 2014

(87) PCT Pub. No.: WO2013/063049
PCT Pub. Date: May 2, 2013

(65) Prior Publication Data
US 2015/0030575 A1 Jan. 29, 2015

Related U.S. Application Data

(60) Provisional application No. 61/550,841, filed on Oct. 24, 2011.

(51) Int. Cl.
*C12N 15/82* (2006.01)
*A61K 38/16* (2006.01)
*A61K 38/26* (2006.01)
*A61K 38/51* (2006.01)
*A61K 38/22* (2006.01)

(52) U.S. Cl.
CPC ........ *C12N 15/8214* (2013.01); *A61K 38/164* (2013.01); *A61K 38/26* (2013.01); *A61K 38/51* (2013.01); *A61K 38/162* (2013.01); *A61K 38/2278* (2013.01); *C07K 2319/55* (2013.01); *Y02A 50/471* (2018.01)

(58) Field of Classification Search
None
See application file for complete search history.

(56) References Cited

U.S. PATENT DOCUMENTS

| | | | |
|---|---|---|---|
| 5,693,507 A | 12/1997 | Daniell | |
| 5,877,402 A | 3/1999 | Maliga | |
| 5,932,479 A | 8/1999 | Daniell | |
| 6,642,053 B1 | 11/2003 | Daniell | |
| 6,680,426 B2 | 1/2004 | Daniell | |
| 7,129,391 B1 | 10/2006 | Daniell | |
| 7,135,620 B2 | 11/2006 | Daniell | |
| 7,294,506 B2 | 11/2007 | Daniell | |
| 7,354,760 B2 | 4/2008 | Daniell | |
| 7,741,536 B2 | 6/2010 | Daniell | |
| 7,767,885 B2 | 8/2010 | Daniell | |
| 7,795,497 B2 | 9/2010 | Daniell | |
| 7,803,991 B2 | 9/2010 | Daniell | |
| 2002/0162135 A1 | 10/2002 | Daniell | |
| 2004/0177402 A1 | 9/2004 | Daniell | |
| 2005/0108792 A1 | 5/2005 | Daniell | |
| 2007/0124830 A1 | 5/2007 | Daniell | |
| 2008/0241916 A1 | 2/2008 | Daniell | |
| 2009/0022705 A1* | 1/2009 | Daniell | C12N 15/8258 424/94.5 |
| 2009/0239795 A1* | 9/2009 | Ballance | C07K 14/57563 514/7.2 |
| 2009/0239796 A1* | 9/2009 | Fineman | A61K 38/26 514/1.1 |
| 2010/0304476 A1 | 2/2010 | Daniell | |
| 2010/0278869 A1 | 4/2010 | Daniell | |
| 2010/0266640 A1* | 10/2010 | Daniell | A61K 39/015 424/261.1 |

FOREIGN PATENT DOCUMENTS

| | | |
|---|---|---|
| WO | 1999010513 | 3/1999 |
| WO | 2001064850 | 9/2001 |
| WO | 2001064927 | 9/2001 |
| WO | 2001064929 | 9/2001 |
| WO | 2001072959 | 10/2001 |
| WO | 2003057834 | 7/2003 |
| WO | 2004005467 | 1/2004 |
| WO | 2004005480 | 1/2004 |
| WO | 2004005521 | 1/2004 |
| WO | 2006027865 | 3/2006 |

(Continued)

OTHER PUBLICATIONS

World Health Organization (2006, Definition and diagnosis of diabetes mellitus and intermediate hyperglycemia: report of a WHO/IDF consultation, Geneva).*
Kwon et al, 2013, Plant Biotechnol. J. 11:77-86.*
Daniell et al., Multigene engineering: dawn of an exciting new era in biotechnology, Curr Opin Biotechnol., 2002, 136-41, 13(2).
Daniell et al., Milestones in chloroplast genetic engineering: an environmentally friendly era in biotechnology, Trends Plant Sci., 2002, 84-91, 7(2).
Watson et al., Expression of Bacillus anthracis protective antigen in transgenic chloroplasts of tobacco, a non-food/ feed crop, Vaccine, 2004, 4374-84, 22(31-32).

(Continued)

*Primary Examiner* — Anne Kubelik
(74) *Attorney, Agent, or Firm* — Kathleen D. Rigaut; Howson & Howson LLP (57) ABSTRACT

Disclosed herein are compositions and methods for treating Type II diabetes. The compositions comprise plant expressed Exendin 4. Particularly exemplified are plant derived compositions that include a CTB-EX4 conjugate that is bioencapsulated in chloroplasts.

17 Claims, 5 Drawing Sheets
Specification includes a Sequence Listing.

(56) References Cited

FOREIGN PATENT DOCUMENTS

| WO | 2007053183 | 10/2007 |
|---|---|---|
| WO | 2008121947 | 10/2008 |
| WO | 2008121953 | 10/2008 |

OTHER PUBLICATIONS

Kumar et al., Plastid-expressed betaine aldehyde dehydrogenase gene in carrot cultured cells, roots, and leaves confers enhanced salt tolerance, Plant Physiol., 2004, 2843-54, 136(1).

Kumar et al., Stable transformation of the cotton plastid genome and maternal inheritance of transgenes, Plant Mol Biol., 2004, 203-16, 56(2).

Quesada-Vargas et al., Characterization of heterologous multigene operons in transgenic chloroplasts: transcription, processing, and translation, Plant Physiol., 2005, 1746-62, 138(3).

Koya et al., Plant-based vaccine: mice immunized with chloroplast-derived anthrax protective antigen survive anthrax lethal toxin challenge, Infect Immun., 2005, 8266-74, 73(12).

Daniell et al., Breakthrough in chloroplast genetic engineering of agronomically important crops, Trends Biotechnol., 2005, 238-45, 23(5).

Limaye et al., Receptor-mediated oral delivery of a bioencapsulated green fluorescent protein expressed in transgenic chloroplasts into the mouse circulatory system, FASEB J., 2006, 959-61, 20(7).

Lee et al., Plastid transformation in the monocotyledonous cereal crop, rice (*Oryza sativa*) and transmission of transgenes to their progeny, Mol Cells., 2006, 401-10, 21(3).

Daniell et al., Chloroplast genetic engineering, Biotechnol J., 2006, 26-33, 1(1).

Verma et al., Chloroplast vector systems for biotechnology applications, Plant Physiol., 2007, 1129-43, 145(4).

Ruhlman et al., Expression of cholera toxin B-proinsulin fusion protein in lettuce and tobacco chloroplasts—oral administration protects against development of insulitis in non-obese diabetic mice, Plant Biotechnol J., 2007, 495-510, 5(4).

Daniell et al., Transgene containment by maternal inheritance: effective or elusive? Proc Natl Acad Sci U S A, 2007, 6879-80, 104(17).

Chebolu et al., Stable expression of Gal/GalNAc lectin of Entamoeba histolytica in transgenic chloroplasts and immunogenicity in mice towards vaccine development for amoebiasis, Plant Biotechnol J., 2007, 230-9, 5(2).

Daniell et al., The complete nucleotide sequence of the cassava (*Manihot esculenta*) chloroplast genome and the evolution of atpF in Malpighiales: RNA editing and multiple losses of a group II intron, Theor Appl Genet., 2008, 723-37, 116(5).

Arlen et al., Effective plague vaccination via oral delivery of plant cells expressing F1-V antigens in chloroplasts, Infect Immun., 2008, 3640-50, 76(8).

Davoodi-Semiromi et al., The green vaccine: A global strategy to combat infectious and autoimmune diseases, Hum Vaccin., 2009, 488-93, 5(7).
Daniell et al., Plant-made vaccine antigens and biopharmaceuticals, Trends Plant Sci., 2009, 669-79, 14(12).
Verma et al., Oral delivery of bioencapsulated coagulation factor IX prevents inhibitor formation and fatal anaphylaxis in hemophilia B mice, Proc Natl Acad Sci U S A, 2010, 7101-6, 107(15).
Verma et al., Chloroplast-derived enzyme cocktails hydrolyse lignocellulosic biomass and release fermentable sugars, Plant Biotechnol J., 2010, 332-50, 8(3).
Ruhlman et al., The role of heterologous chloroplast sequence elements in transgene integration and expression, Plant Physiol., 2010, 2088-104, 152(4).
Davoodi-Semiromi et al., Chloroplast-derived vaccine antigens confer dual immunity against cholera and malaria by oral or injectable delivery, Plant Biotechnol J., 2010, 223-42, 8(2).

* cited by examiner (a)

Hinge
GPGPRRKRHGEGTFTSDLSKQMEEEAVRLFIEWLKNGGPSSGAPPPS
↑
Furin cleavage site (b)

Figure 3:
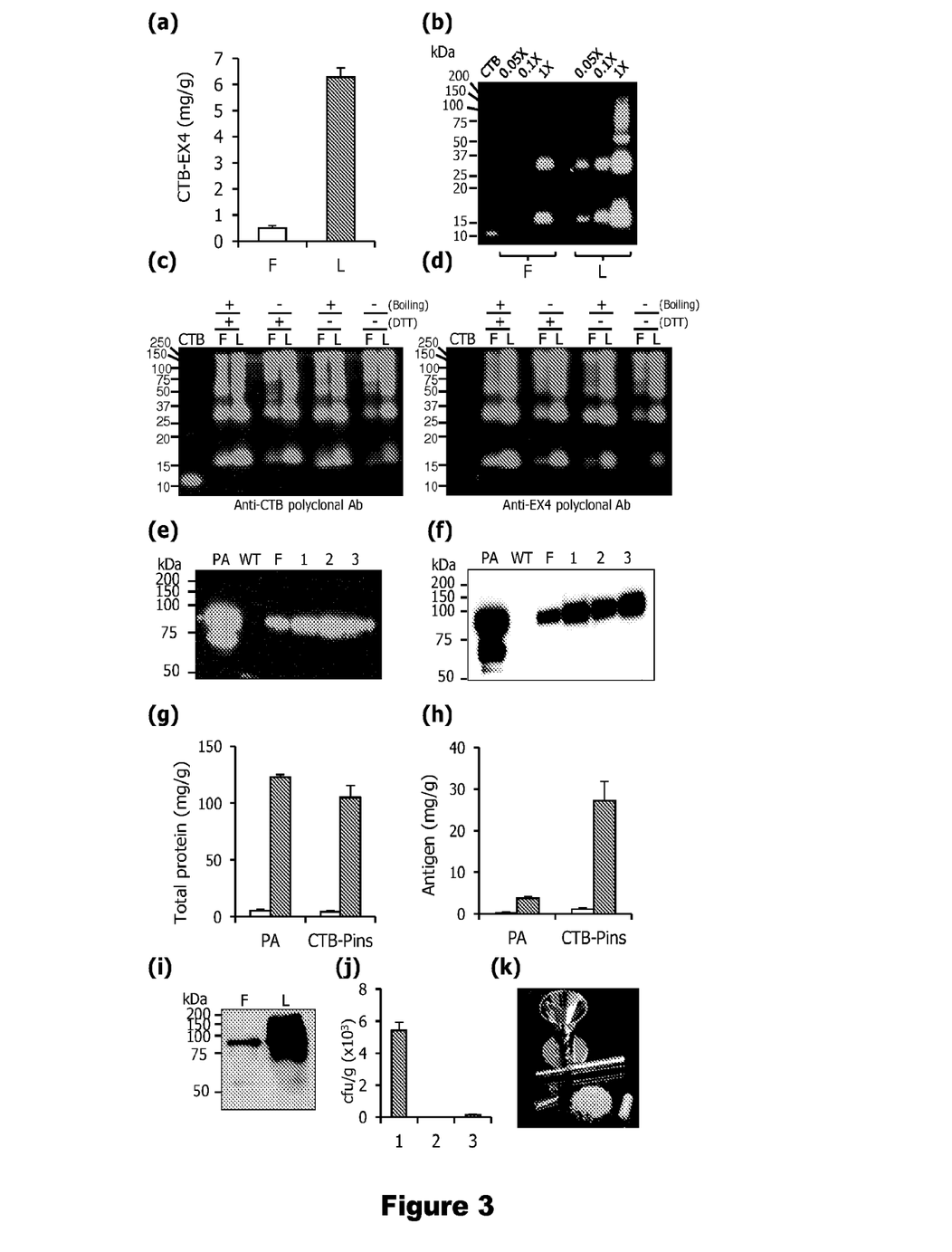

SEQUENCE LISTING

```
<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Hinge region

<400> SEQUENCE: 1

Gly Pro Gly Pro
1
```

```
<210> SEQ ID NO 2
<211> LENGTH: 4
<212> TYPE: PRT
<213> ORGANISM: Artificial Sequence
<220> FEATURE:
<223> OTHER INFORMATION: Furin cleavage site

<400> SEQUENCE: 2

Arg Arg Lys Arg
1

<210> SEQ ID NO 3
<211> LENGTH: 30
<212> TYPE: DNA
<213> ORGANISM: Artificial Sequence
<220> FEATURE:
<223> OTHER INFORMATION: DV42 primer

<400> SEQUENCE: 3
ttcatatgac acctcaaaat attactgatt                                    30

<210> SEQ ID NO 4
<211> LENGTH: 60
<212> TYPE: DNA
<213> ORGANISM: Artificial Sequence
<220> FEATURE:
<223> OTHER INFORMATION: R1-EX4 primer

<400> SEQUENCE: 4
catttgttta gataaatcag aagtgaaagt accttcacca tgacgtttac gccggggccc   60

<210> SEQ ID NO 5
<211> LENGTH: 60
<212> TYPE: DNA
<213> ORGANISM: Artificial Sequence
<220> FEATURE:
<223> OTHER INFORMATION: R2-EX4 primer

<400> SEQUENCE: 5 ccgttttta accattcaat gaataaacgt acagcttctt cttccatttg tttagataaa   60

<210> SEQ ID NO 6
<211> LENGTH: 60
<212> TYPE: DNA
<213> ORGANISM: Artificial Sequence
<220> FEATURE:
<223> OTHER INFORMATION: R3-EX4 primer

<400> SEQUENCE: 6
agttctagat caagaaggag gaggagcacc agaagaagga ccaccgtttt ttaaccattc   60

<210> SEQ ID NO 7
<211> LENGTH: 47
<212> TYPE: PRT
<213> ORGANISM: Artificial Sequence
<220> FEATURE:
<223> OTHER INFORMATION: Synthetic sequence

<400> SEQUENCE: 7

Gly Pro Gly Pro Arg Arg Lys Arg His Gly Glu Gly Thr Phe Thr Ser
1               5                   10                  15

Asp Leu Ser Lys Gln Met Glu Glu Glu Ala Val Arg Leu Phe Ile Glu
            20                  25                  30

Trp Leu Lys Asn Gly Gly Pro Ser Ser Gly Ala Pro Pro Pro Ser
        35                  40                  45
```

ORALLY ADMINISTERED PLASTID EXPRESSED CHOLERA TOXIN B SUBUNIT-EXENDIN 4 AS TREATMENT FOR TYPE 2 DIABETES

CROSS-REFERENCE TO RELATED APPLICATIONS

This application is a § 371 national phase entry of International Patent Application PCT/US2012/061598, filed Oct. 24, 2012, which claims priority to U.S. Provisional Application No. 61/550,841 filed Oct. 24, 2011, the entire contents of each being incorporated by reference herein as though set forth in full.

STATEMENT OF FEDERAL FUNDED RESEARCH

This invention was made with government support under grant numbers 2009-39200-19972 and 2010-39200-21704 awarded by the US Department of Agriculture and GM063879 awarded by the National Institutes of Health. The government has certain rights in the invention.

BACKGROUND

Peptides, as therapeutic agents, have several advantages in clinical applications due to their low toxicity and high specificity (Bellmann-Sickert and Beck-Sickinger, 2010). Recently the US Food and Drug Administration (FDA) approved several peptide drugs including Enfuvirtide that inhibits HIV entry into cells, Exenatide that stimulates insulin secretion in type 2 diabetes patients and several peptides for treatment of cancer (Bellmann-Sickert and Beck-Sickinger, 2010). Despite these advantages, therapeutic peptides have several limitations. They are highly prone to proteolytic degradation during storage or when used for oral administration (McGregor, 2008) and require parenteral administration. In addition, these peptides need cold storage due to short shelf life after purification or chemical synthesis. Moreover, repeated injections are often needed but this decreases patient compliance (Hamman and Steenekamp, 2011). Therefore, it has been discovered herein that there is a great need for exploration of less expensive and patient-friendly drug delivery methods.

Type 2 diabetes is caused by combination of beta cell dysfunction and insulin resistance (Scheen, 2003). It is predominantly diagnosed in adults and responsible for 90-95% of the existing diabetic cases (National diabetes fact sheet, 2011). Surplus production of hepatic glucose and reduced uptake of glucose also contribute to excess blood sugar levels (Scheen, 2003). The type 2 diabetic patients exhibit belittled incretin effect, which requires insulin secretion in response to high glucose in the blood (Scheen, 2003). Diabetes is a global rising problem. According to the national diabetes fact sheet 2011, the total cost associated annually for treatment and management of diabetes in the US is $116 billion whereas the indirect costs associated with loss of work, disability and other factors was $58 billion adding up the total cost to $174 billion. The treatment for diabetes includes either oral drugs (small molecules) with or without insulin injections. Globally, the prevalence of diabetes is estimated to escalate from 171 million in 2000 to 366 million in 2030 (Davidson, 2009), which could double the associated costs. Diabetes is a major health and economic burden on society (Wild et al., 2004) and therefore the cost of treatment of diabetes should be addressed.

GLP-1 is a peptide hormone secreted by the L cells of the intestine that stimulates the secretion of insulin from the pancreas (Chia et al., 2005). It has been shown to play an important role in increasing the beta cell mass and has potent antidiabetic effects associated with weight loss (Baggio and Drucker, 2007). But GLP-1 has a very short half-life of less than 2 min because it is degraded by the dipeptidyl peptidase IV (DPP-IV) serum enzyme into biologically inactive form, thereby lowering the incretin action of the peptide (Kieffer et al., 1995). Thus, it is disclosed herein that DPP-IV resistant GLP-1 analogs are needed for treatment of the type 2 diabetes.

EX4 is a DPP-IV resistant analog of GLP-1 with higher binding efficacy to the mammalian GLP-1 receptor than GLP-1 and functions as an effective agonist (Young et al., 1999). EX4 modulates the glucose level in a glucose dependent manner and increases the sensitivity to insulin and has shown promising biological activities in vivo for treating type 2 diabetes (Young et al., 1999). Exenatide, a synthetic EX4 is the first drug that carries out the function of incretin to be approved by FDA for glycemic control, along with an oral antidiabetic medication. Exenatide is used in injectable form and requires cold storage and sterility. In addition, the requirement for multiple injections decreases patient compliance. Thus, it is disclosed herein that there is a need for alternative methods of production and delivery of EX4 or other therapeutic proteins to reduce the cost and increase patient compliance.

BRIEF DESCRIPTION OF THE DRAWINGS

FIG. 1 Evaluation of transgene integration. (a) Schematic representation of the flanking sequence probe (0.81 kb) and expected products of the untransformed and transplastomic tobacco chloroplast genome when digested with HindIII (H). Southern blot probe was generated using BamHI (B) and BglII (B'). Primers used for transgene amplification are represented by arrows. Amino acid sequence (SEQ ID NO: 7) indicates the hinge, furin cleavage site, and EX4 (bold letter). Asterisk represents resistant amino acid against DPP-IV. C-terminal 9-amino acid is represented by dotted line. (b) The amplification of genomic DNA fragment with 3P/3M and 5P/2M primer sets to check transgene integration. M, DNA size marker; WT, untransformed; #5, 6, and 9, transplastomic lines; Ve, CTB-EX4 containing pLD vector. (c) Southern blot analysis of CTB-EX4 transplastomic lines showing homoplasmy.

FIG. 2 Quantification and functional evaluation of CTB-EX4. Western blot analysis of total leaf homogenate (H, 5 μg) and soluble (S, 5 μg) protein probed with anti-CTB (a) or anti-EX4 (b) antibodies. Lane 1, 6.25; 2, 12.5; 3, 25 ng of purified cholera toxin B subunit; +, with DTT; −, without DTT; #6 and 9, CTB-EX4 transplastomic lines; WT, untransformed. (c) Percentage of CTB-EX4 in the total leaf protein from mature leaves at different harvesting time. (d) GM1 ELISA assay for evaluation of CTB-EX4 pentamer assembly. CTB, positive control (10 ng); F, fresh leaf; L, lyophilized CTB-EX4 transplastomic plant extracts (5 μg of total leaf protein), respectively; WT, untransformed total leaf protein (5 μg), BSA, negative control. Data shown are means±SD of three independent experiments.

FIG. 3 Lyophilization and characterization. (a) Amount of CTB-EX4 protein in fresh (F) and lyophilized (L) leaves. (b) Western blot analysis of fresh and lyophilized leaves expressing CTB-EX4. Equal quantity (50 mg) of fresh and lyophilized material was extracted in same volume (300 μl) of extraction buffer. Samples were loaded in a serial dilution as indicated. Western blot analysis with anti-CTB (c) and anti-EX4 (d) polyclonal antibody to evaluate long-term stability of lyophilized CTB-EX4 after storage at room temperature for 10 months. F, fresh leaf; L, 10-month old lyophilized leaf. Total leaf protein (5 µg) was loaded in each lane. CTB, Positive or negative control (20 ng). Samples were incubated for 10 min with DTT (100 mM) or boiled for 2 minutes. (e) Western blot analysis to evaluate stability of PA in lyophilized lettuce leaves after storage at room temperature for 2 (1), 4 (2), and 6 (3) months. PA, standard (100 ng), WT, untransformed lettuce. Total soluble protein (3 µg) was loaded in each lane. (f) Antigen stability after 3 months of storage, and lyophilization for different durations: (1) 24, (2) 48 and (3) 72 hrs. Fold increase of total protein (g) and specific antigen (h) after lyophilization. PA, lettuce transplastomic plant expressing PA; CTB-Pins, lettuce transplastomic plant expressing CTB-Proinsulin; white bar, fresh material; grey bar, lyophilized material. (i) Western blot analysis of fresh (F) and lyophilized (L) leaves expressing PA. Total soluble protein (10 µl) was loaded after equal quantity (50 mg) was extracted in same volume (300 µl) of extraction buffer. (j) Microbial burden of leaves expressing PA. 1, fresh leaf; 2, lyophilized leaf; 3, commercially available freeze-dried alfalfa capsules. (k) Simplified diagram of capsulation of lyophilized transplastomic leaf material. Data shown are means±SD of three independent experiments.

Figure 4:
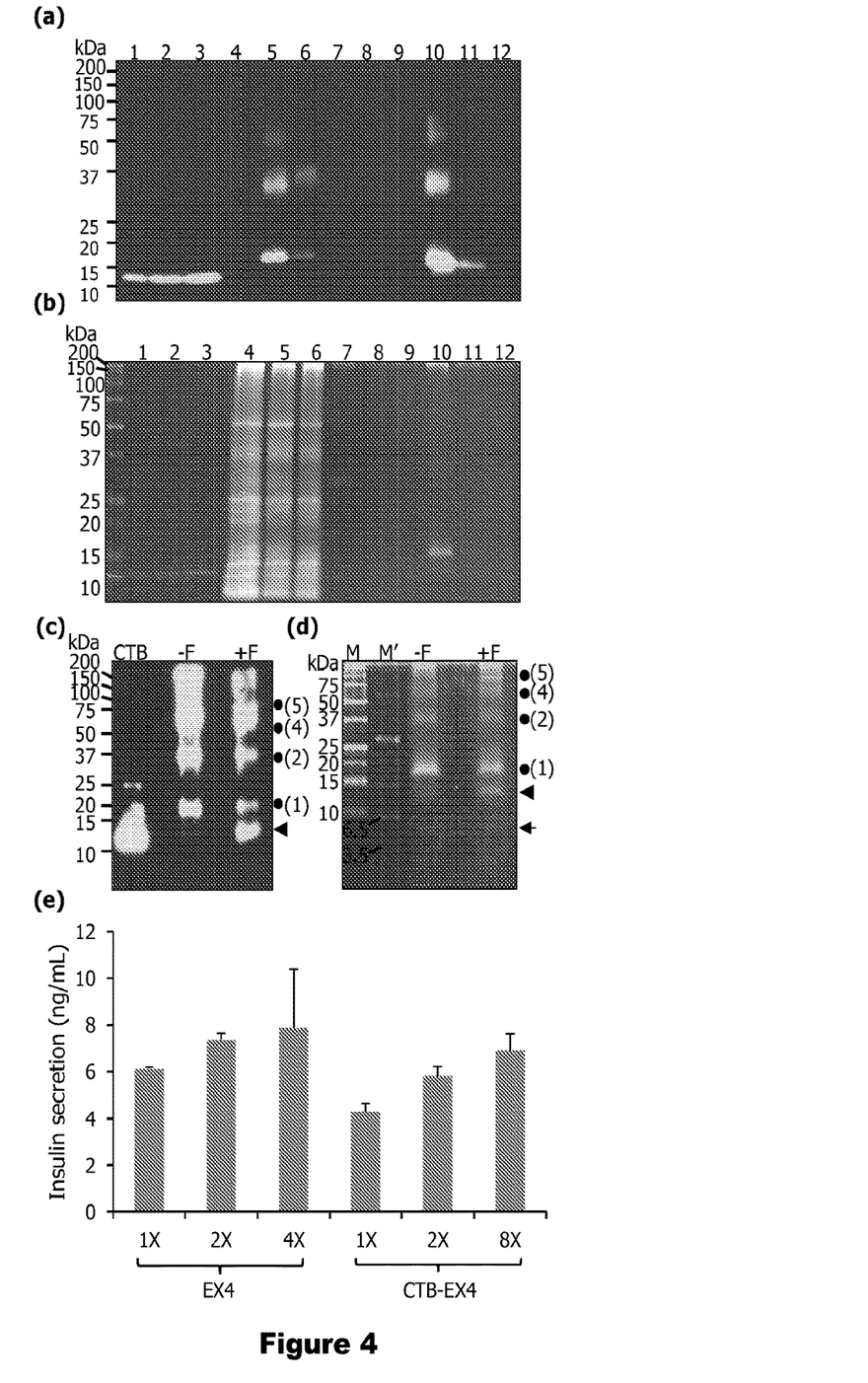

FIG. 4 Purification of CTB-EX4 and pancreatic cell line assay. Western blot (a) and silver staining (b) of purified CTB-EX4. 1-3, CTB standard proteins of 12.5, 25, and 37.5 ng; 4, wild type total leaf protein (5 µg); 5, soluble fraction of CTB-EX4 before purification (5 µg); 6, soluble fraction of CTB-EX4 after purification (5 µg); 7-9, washed fractions; 10-12, elution fractions. (c, d) Furin cleavage assay of purified CTB-EX4. CTB, standard (25 ng); −F, without furin; +F, with furin; M, protein size marker; M', ultra-low range protein size marker; arrow head, cleaved CTB (12.7 kDa); arrow, cleaved EX4 (4.2 kDa); dots and numbers, locations of monomer and oligomers of CTB-EX4. Proteins were resolved on 12% (c) and 16% (d) of Tricine-SDS-PAGE. (e) Mouse pancreatic cell line assay. Commercial EX4 (1×=5 nM) and partially purified CTB-EX4 (1×=32 nM, concentration based on the molecular weight of the CTB) were added to beta-TC6 cells. The graph was normalized to PBS value which was used as a negative control. Insulin secretion was compared at three different concentrations in each group, with duplicate samples, using 88 wells of insulin detection kit. Data shown are means±SD (n=6).

Figure 5:
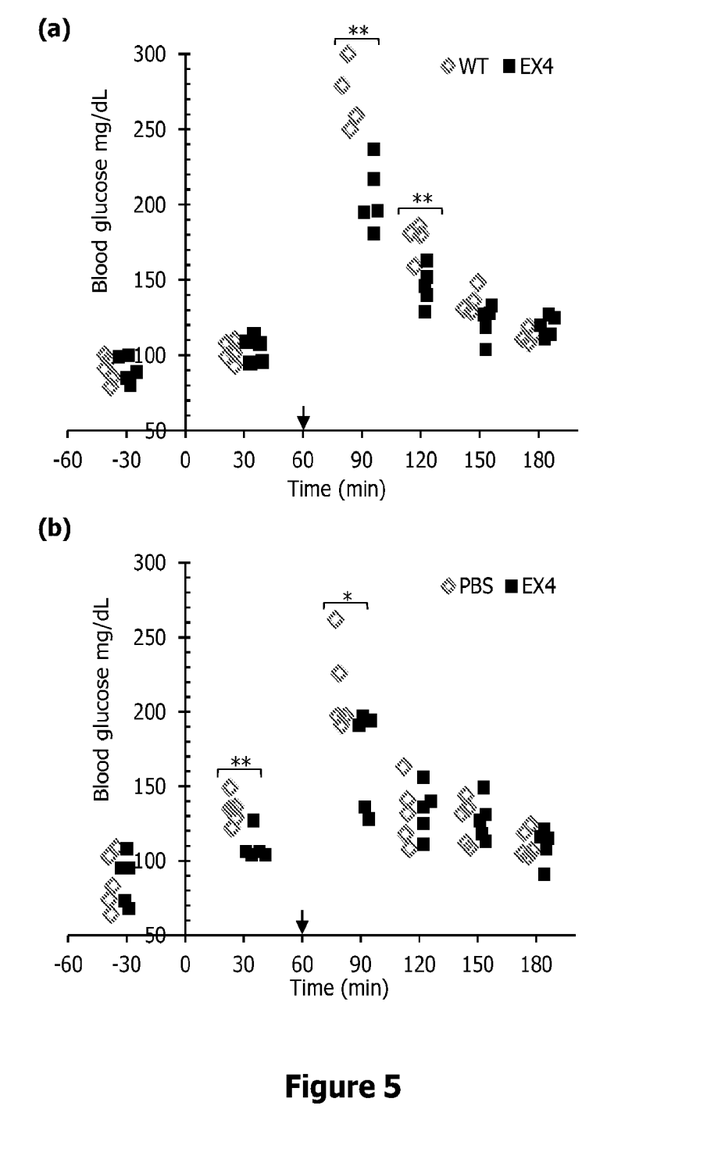

FIG. 5 Evaluation of functionality of CTB-EX4 in mice after oral gavage or injection. Glucose (2 g/kg body weight) was injected intraperitoneally at t=60 (arrows). (a) Mice were orally gavaged with lyophilized untransformed (WT) and CTB-EX4 plant leaf materials (EX4) at t=0. One outlier was removed from control group because of no glucose spike at t=90. (b) Mice were given i.p. injection of PBS (200 µl) and commercial EX4 resuspended in PBS (0.01 µg in 200 µl) at t=0. Glucose measurements were made 2 or 3 times for each mouse, for a total of 288 evaluations of blood glucose levels in mouse sera. Single factor ANOVA was performed to test significant difference between groups statistically. *$P<0.05$, **$P<0.01$.

DETAILED DESCRIPTION

It is demonstrated in the present disclosure that a chloroplast transformation system and bioencapsulation within plant cells would be cost effective for the production and delivery of functional exendin-4 (EX4) for treatment of type 2 diabetes. In particular, the present disclosure describes the oral delivery of transplastomic lyophilized leaf materials comprising a EX4 protein, stability of foreign proteins after prolonged storage at room temperature, ability to deliver appropriate dosage for treating diabetes, consistency and preservation of the integrity of the heterologous protein, and microbial contamination in plant materials.

The use of plant chloroplasts to produce therapeutic proteins is emerging as an alternative new technology in order to reduce their cost of production by elimination of purification, cold storage, transportation, sterile delivery and by extension of their shelf life (Daniell, 2007, Arntzen, 2008; Yusibov et al., 2011). The chloroplast technology integrates transgenes into the chloroplast genome through homologous recombination (Verma et al., 2008). The concept offers several advantages over nuclear transformation (Ruhlman et al., 2007; Boyhan and Daniell, 2011; Daniell et al., 2009a). The maternal inheritance of chloroplast genomes and harvesting leaves before flowering offer important biological containment strategies (Daniell, 2007). In addition, overcoming the transgene silencing and position effect through site specific recombination minimizes the number of events required for screening (Verma et al., 2008). Other proteins have been expressed in plant chloroplasts including insulin like growth factor (Daniell et al., 2009b), interferon α2b (Arlen et al., 2007), coagulation factor IX (Verma et al., 2010), proinsulin (Ruhlman et al., 2007), antimicrobial peptides (Lee et al., 2011), human transforming growth factor-β3 (Gisby et al., 2011), and vaccine antigens against viral, bacterial, and protozoan pathogens (Davoodi-Semiromi et al., 2010; Fernandez-San Millán et al., 2008; Koya et al., 2005). However, it is believed that the present application and parent application represent the first demonstration of successfully expressing an EX4 protein, and use of such protein to successfully treat diabetes.

According to one embodiment, provided herein is a plant cell of a plant, wherein said plant cell comprises chloroplasts transformed to express CTB-Exendin (e.g., Exendin 4). In a specific embodiment, the plant cell is edible.

In another embodiment, disclosed herein is an orally-administrable composition comprising CTB-Exendin expressed in a chloroplast; and rubisco. The chloroplast may be from an edible plant. Examples of edible plants include plants that are edible without cooking, i.e., edible without the need to be subjected to heat exceeding 120 degrees Fahrenheit for more than 5 min Examples of such edible plants include, but are not limited to, *Lactuca sativa* (lettuce), apple, berries such as strawberries and raspberries, citrus fruits, tomato, banana, carrot, celery, cauliflower; broccoli, collard greens, cucumber, muskmelon, watermelon, pepper, pear, grape, peach, radish and kale. In a specific embodiment, the edible plant is *Lactuca sativa*.

According to another embodiment, disclosed herein is a sample of CTB-Exendin bioencapsulated in chloroplasts of a plant cell. In a specific aspect, the plant cell is from an edible plant. In another related embodiment, the plant cell is homoplasmic with respect to plant plastids transformed to express said CTB-Exendin.

According to another embodiment, disclosed herein is a *Lactuca sativa* plant plastid comprising a plastid genome transformed with a heterologous DNA coding sequence encoding a CTB-Exendin, and integrated into said plastid genome such that said CTB-Exendin is expressed in and present in said plastid. In a related embodiment, the *Lactuca*

*sativa* plant cell is homoplasmic with respect to plastids transformed to express a CTB-exendin.

Figure 1:
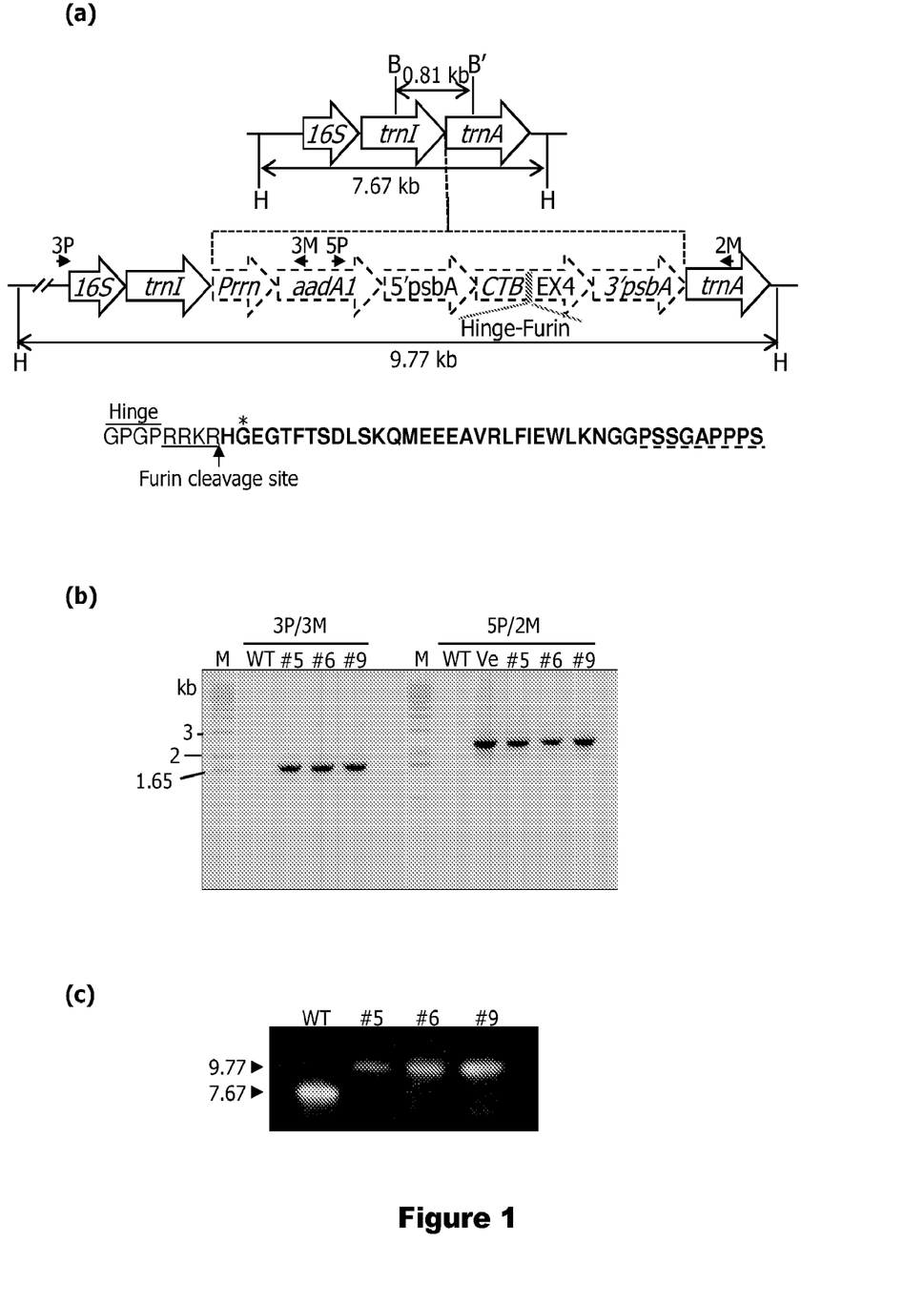
Figure 2:
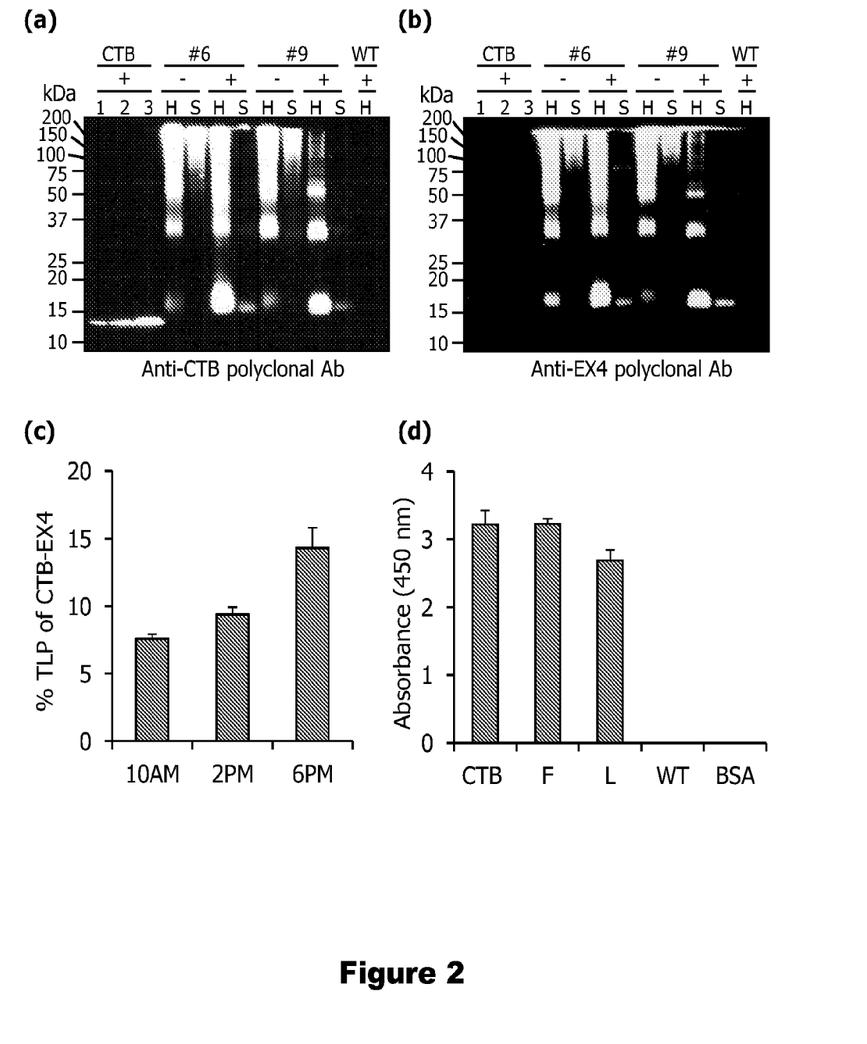

In a further embodiment, provided is a method of retarding the development of or treating Type II diabetes in a subject in need thereof comprising administering to said subject a composition comprising a CTB-Exendin polypeptide expressed in a chloroplast in a plant and, optionally, a plant remnant. The plant remnant may be rubisco. The subject in need typically exhibits at least one symptom comprising ketoacidosis, a state of metabolic dysregulation characterized by the smell of acetone; a rapid, deep breathing known as Kussmaul breathing; nausea; vomiting and abdominal pain; polyuria (frequent urination); polydipsia (increased thirst); polyphagia (increased hunger), increased or decreased insulin levels, or elevated serum glucose. In a related embodiment, the subject in need exhibits impaired glucose tolerance. In another related embodiment, the subject in need exhibits fasting glucose levels from 100 to 125 mg/dL (5.6 to 6.9 mmol/L). In a further related embodiment, the subject in need is exhibits plasma glucose at or above 140 mg/dL (7.8 mmol/L), but not over 200 mg/dL (11.1 mmol/L), two hours after a 75 g oral glucose load.

An additional embodiment relates to a composition for retarding the development of or treating diabetes comprising a therapeutically effective amount of a CTB-Exendin polypeptide and a plant remnant, such as from *Lactuca sativa*.

A plant remnant may include one or more molecules (such as, but not limited to, proteins and fragments thereof, minerals, nucleotides and fragments thereof, plant structural components, etc.) derived from the plant in which the protein of interest was expressed. A plant remnant may include plant material such as whole or portions of plant leafs, stems, fruit, roots, etc. A plant remnant may pertain to a crude plant extract. The plant extract can be considered a plant remnant as well as molecules found within the plant extract. In a specific embodiment, the plant remnant is rubisco.

In yet a further embodiment, disclosed herein is a plastid transformation and expression vector for transformation of *Lactuca sativa* plastid, said vector comprises an expression cassette comprising, as operably linked components in the 5' to the 3' direction of translation, a promoter operative in said plastid, a selectable marker sequence, a heterologous polynucleotide sequence coding a CTB-Exendin protein, transcription termination functional in said plastid, and flanking each side of the expression cassette, flanking DNA sequences which are homologous to a DNA sequence of the target plastid genome, whereby stable integration of the heterologous coding sequence into the plastid genome of the target plant is facilitated through homologous recombination of the flanking sequence with the homologous sequences in the target plastid genome. In a related embodiment, the plastid is selected from the group consisting of chloroplasts, chromoplasts, amyloplasts, proplastide, leucoplasts and etioplasts. In another related embodiment, the selectable marker sequence is an antibiotic-free selectable marker.

Plants stably transformed to include a plastid stably transformed with vectors described herein, or the progeny thereof, including seeds is disclosed.

EXAMPLES

Example 1

Creation and Characterization of CTB-EX4 Transplastomic Lines

CTB-EX4 fusion gene was constructed in the chloroplast transformation vector—pLD, with a GPGP (Gly-Pro-Gly-Pro; SEQ ID NO: 1) hinge region to minimize steric hindrance of the fused EX4 and furin cleavage site, RRKR (Arg-Arg-Lys-Arg; SEQ ID NO: 2), for its release into blood after the fusion protein is internalized into epithelial cells (FIG. 1*a*). EX4 is a 39-amino acid peptide identified in the salivary gland of lizard, *Heloderma suspectum* and has 53% homology of amino acid with GLP-1 but it has several distinct features from GLP-1. N-terminal sequence (His-Gly-Glu) of EX4 (FIG. 1*a*) is resistant to DPP-IV which rapidly cleaves the corresponding GLP-1 sequence (His-Ala-Glu) (Doyle et al., 2003). In addition, C-terminal 9-amino acid sequence of EX4 (FIG. 1*a*), which is absent from GLP-1, showed biological importance. Its truncated form, EX4 (1-30), has 10 times less binding affinity to GLP-1 receptor, which is similar to that of GLP-1 (Doyle et al., 2003). Many of substrate sequences to endopeptidase are present in GLP-1 but not in EX4 (Hupe-Sodmann et al., 1995). These features make the EX4 5,500 times more potent GLP-1 receptor agonist than GLP-1 (Davidson, 2009). Therefore, EX4 was chosen for expression in plant chloroplasts. The fusion gene was driven by the psbA promoter and 5' untranslated region (UTR) to increase expression and the transcript was stabilized by the psbA 3' UTR. The cloned CTB-EX4 fusion gene into the chloroplast vector was fully sequenced before bombardment. The putative transplastomic lines were confirmed for transgene integration using the primer sets which were able to anneal specifically to complementary sequences of transgene cassette and the chloroplast genome. PCR results showed products of expected sizes as a result of amplification for the defined region with those primers, 1.65 kb with 3P/3M and 2.1 kb with 5P/2M (FIG. 1*b*). The site specific integration of the CTB-EX4 gene was further confirmed using Southern blot analysis, by probing with the trnI and trnA flanking sequence. Three Hind III restricted independent transplastomic lines showed distinct hybridizing fragments of 9.77 kb (FIG. 1*c*) but not the 7.67 kb fragment from wild type. Thus Southern blot analysis confirmed the site specific and stable integration of the transgenes into the chloroplast genome and homoplasmy.

Example 2

Characterization of CTB-EX4 Fusion Protein Expressed in Chloroplasts

To investigate proper translation of the two genes within chloroplasts, specific antibodies against CTB or EX4 were used. Both of the antibodies detected the expected fusion protein of correct size, with no cross-reacting proteins from untransformed plants. As expected, the detected band pattern was identical to each other (FIG. 2*a, b*). In addition, there was no cross detection of CTB standard proteins by anti-EX4 antibody (FIG. 2*b*). Each CTB monomer has an intramolecular disulfide bond. Extensive interactions between monomers (hydrogen bonds, salt bridges, and hydrophobic interactions) are responsible for the stable pentameric structure of CTB (Sanchez and Holmgren, 2008). But this integrity was disrupted when reducing agents were included in the extraction buffer (FIG. 2*a, b*) in which much more monomeric form of CTB-EX4 was observed, when compared with the extraction without the reducing agent. Moreover, much less of the fusion protein was detected in the soluble fraction (FIG. 2*a, b*). The expression level of the fusion protein was measured quantitatively using densitometry with known amount of CTB protein to generate standard curve (Figure S1) at different time points. The range of expression varied between 7.6% and 14.3% of TLP (FIG. 2c). When the ability of CTB-EX4 fusion protein to bind to the GM1 receptor was evaluated by GM1 ELISA, the absorbance values were similar to the CTB positive control. This indicates that there was proper folding and disulfide bond formation that are required for the formation of the pentameric structure of CTB-EX4 (FIG. 2d).

Example 3

Stability, Folding, Dosage, Microbes in Lyophilized Materials after Prolonged Storage In this study, lyophilized leaf material (6.26 mg of CTB-EX4/g) was used to deliver appropriate dose of CTB-EX4 by oral gavage in mice. The content of CTB-EX4 increased 12.5 fold when compared to fresh leaf material (0.5 mg of CTB-EX4/g) (FIG. 3a) and significant difference in CTB-EX4 intensity was also observed with equal loading of proteins (equal weight) from fresh and lyophilized plant materials, in a serial dilution (FIG. 3b), further confirming quantitative studies. The functionality of the lyophilized fusion protein was confirmed using GM1 ELISA and western blot assays. In the immunoblots with the separation range of 10-250 kDa, use of specific polyclonal antibodies against CTB, EX4, and PA did not detect any cleaved fragments for each lyophilized protein in, providing evidence for their stability. The comparable absorbance of lyophilized CTB-EX4 to CTB standard was detected (FIG. 2d) and oligomeric forms of CTB were also detected (FIG. 3b). These results indicate that lyophilization does not affect the assembly of CTB pentamer. In this study, lyophilized leaves stored up to 4 months at room temperature did not show any degraded CTB-EX4 protein. To investigate long-term stability of CTB-EX4 further, 10 month-old lyophilized leaf material was compared with fresh leaves in different conditions using western blots. Detected band patterns between fresh and lyophilized protein samples were identical, including formation of pentamers or oligomers (FIG. 3c, d). Furthermore, the relative band intensity between CTB-EX4 monomers of lyophilized samples gradually increased with denaturation (by boiling and/or addition of DTT, FIG. 3d). Relative decrease of the monomer intensity was 100 (+ and +, boiling and DTT, respectively), 66 (− and +), 40 (+ and −), and 7.8% (− and −) (FIG. 3d). This demonstrated that pentameric structure of CTB-EX4 can be stably maintained in lyophilized state for a long time at room temperature.

To evaluate stability of therapeutic proteins after long-term storage of lyophilized materials at room temperature, transplastomic lettuce expressing the protective antigen (PA) from *Bacillus anthracia* and CTB fused proinsulin (CTB-Pins) were investigated. The reason for investigating stability of other proteins unrelated to this project is to evaluate the reproducibility of this concept and to evaluate stability of much larger size proteins (EX4 is ~4.2 kDa whereas the Anthrax protective antigen is ~83 kDa). The soluble PA is stable up to 6 months of storage at room temperature in lyophilized leaves with no apparent cleaved products similar to fresh material (FIG. 3e). Further study showed that PA is stable in lyophilized lettuce stored at room temperature for more than 15 months (data not shown). The duration of lyophilization did not affect the stability of PA (FIG. 3f) but optimal dehydration was achieved after 72 hrs dehydration. Concentration of both PA and CTB-Pins increased 24 fold in lyophilized leaves when compared to fresh transplastomic materials (FIG. 3h). The fold increase of total leaf proteins was also similar to that of the antigens when compared to fresh material (FIG. 3g). Much more intense band against PA was observed over the fresh material in western blots when equal mass of samples were loaded (FIG. 3i), further confirming quantitative studies.

Bacterial contamination was investigated between fresh and lyophilized materials to facilitate the safe oral delivery. For comparison, commercially available freeze-dried alfalfa was used as control. While fresh lettuce leaves contained up to ~6,000 cfu/g microbes, lyophilized leaves expressing various foreign proteins had no detectable microbes, when plated on different growth media (FIG. 3j). These investigations show that highly concentrated therapeutic peptides or proteins could be delivered orally and safely, when the lyophilized leaf material is used in capsules (FIG. 3k).

Example 4

Purification and Characterization of Transplastomic EX4

The CTB-EX4 fusion protein was purified with the anti-CTB antibody conjugated to protein A beads. The immunoblot assay against purified CTB-EX4 showed that the first elution fraction contained the highest amount of fusion protein and densitometric analysis of the first elution of purification revealed 73% purity (FIG. 4a). Silver stained gel showed a prominent single band, which corresponded to the CTB-EX4 band in the western blot (FIG. 4b). Then furin cleavage assay was performed with the purified fusion protein to check if the oral delivery of proteins would result in cleavage of transplastomic proteins by the furin enzyme, which is present ubiquitously in all cell and tissue types in the body (Limaye et al., 2006). The furin treated sample revealed the presence of an additional polypeptide at ~12.7 kDa, which represents the size of CTB monomer subunit (including 8 amino acids for the hinge and furin cleavage site) without EX4 fusion (FIG. 4c, d) indicating the furin cleavage site introduced in the construct was functional. The silver stain revealed two cleavage products, one at ~12.7 kDa representing the same size of cleaved CTB product as in FIG. 4c and a faint band at ~4.2 kDa representing the EX4 monomer (FIG. 4d). These results confirmed accessibility of furin to its cleavage site to release EX4 after the fusion protein is internalized, by binding to GM1 receptor present on the intestinal epithelium cell surface.

Example 5

In Vitro Beta-TC6 Pancreatic Cell Line Assay to Evaluate Insulin Secretion

For functional evaluation of CTB-EX4, purified fusion protein was incubated with beta-TC6 cells, mouse pancreatic cell line harboring GLP-1 receptor on their surface. The role of the receptor is to amplify glucose-dependent insulin secretion. In a previous report, beta-TC6 cells increased insulin secretion in response to glucose concentration in a range from 0 to 20 mM. The insulin secretion was further enhanced when EX4 was added within the range of glucose (Masure et al., 2005). In this study, single glucose concentration (10 mM) was chosen to investigate the enhancement of insulin secretion by increasing the concentration of CTB-EX4. Direct comparison of commercial EX4 with purified CTB-EX4 for insulin secretion was inadequate due to a different molecular weight and a fusion protein. Therefore, the amount of secreted insulin was compared by increasing concentration of each protein in a dose dependent manner Indeed beta cells treated with different levels of purity of CTB-EX4 (crude plant extract, partial and total purification) were evaluated in 88 wells of the insulin ELISA detection kit for optimization and several independent investigations. We compared insulin secretion between commercial EX4 and purified CTB-EX4 at three different concentrations using 88 wells of insulin detection kit. All independent investigations confirmed that purified CTB-EX4 showed insulin secretion activity similar to commercial EX4. For control PBS was used instead of CTB alone because commercial CTB is purified from *E. coli* and it exists as a monomer. But chloroplast-derived CTB-EX4 exists in pentameric form (required for $GM_1$ binding) or other oligomeric forms as seen in FIG. 2a and b. Therefore, commercial CTB does not serve as an appropriate control. Insulin secretion reached its maximum at the concentration of 4× when treated with commercially available EX4 peptide, which is consistent with a previous report (Baggio et al., 2004) Likewise, purified CTB-EX4 also increased insulin secretion in a concentration dependent manner (FIG. 4e). Therefore, this result indicates similar functionality of EX4 when fused with CTB expressed in plant chloroplasts or when EX4 was chemically synthesized.

Example 6

Oral Delivery of Lyophilized CTB-EX4 Transplastomic Leaves to Mice Lowered Blood Glucose Level In order to investigate the potential for lowering blood glucose level after oral delivery of lyophilized CTB-EX4 leaf material, blood glucose level was tested in mice after glucose spike by intraperitoneal injection. In three previous independent tests, CTB-EX4 showed its function of lowering glucose level at 90 min after oral gavage, even without glucose spike (data not shown). For evaluation of orally delivered lyophilized CTB-EX4 effect on glucose level, blood glucose levels were measured in mice sera at different time points using 288 glucose test strips for optimizing this system, with or without glucose spike and overnight fasting. Glucose measurements were made 2 or 3 times for each mouse, for a total of 288 evaluations of blood glucose levels in mouse sera. Administered dosage was calculated for each method. $2.39 \times 10^{-6}$ mole of EX4 per mouse (0.01 μg/4.19 kDa, MW of EX4) was used for i.p. injection, while $1.2 \times 10^{-2}$ mol of lyophilized EX4-CTB per mouse (208.5 μg/17.2 kDa, MW of CTB-EX4) was delivered orally. To evaluate glucose lowering potential by CTB-EX4, blood glucose level of mice was spiked intraperitoneally at 60 min after oral gavage. Glucose lowering effect of CTB-EX4 reached maximum up to 24.8% reduction at t=90 (FIG. 5a). As the duration after oral gavage increased, the glucose lowering effect became smaller (17.3% at t=120, and 10.1% at t=150) then finally came down to similar level to control group at t=180 (FIG. 5a), due to the normal functional pancreas. To compare the potency of chloroplast derived CTB-EX4 with synthetic EX4 peptide in terms of glucose lowering effect, mice were subject to same procedure as in FIG. 5a except for i.p. injection of EX4 peptide instead of oral gavage of CTB-EX4 plant material. Similar glucose lowering effect (21.8% reduction) was observed at t=90 as oral gavage (FIG. 5b). Taken together, oral administration of lyophilized CTB-EX4 fusion protein produced in plant chloroplast functions as well as if not better than commercial purified EX4 peptide.

Discussion Related to Examples 1-6

Type 2 diabetes affects a vast majority of the global population and requires cost effective treatment, which otherwise poses the threat of becoming a pandemic (National diabetes fact sheet, 2011). Exenatide, an injectable insulinotropic agent demonstrates appreciable antidiabetic effects in clinical use among type 2 diabetes patients (Lovshin and Drucker, 2009; Riddle et al., 2006) but requires cold storage and injections. This kind of subcutaneous injection in the abdomen is very inconvenient for patient because injection sites should be cleaned with alcohol before use and/or rotated to avoid or minimize skin irritation (Barnhart et al., 2011). In this study, we report the expression of CTB fused EX4 in chloroplast and its functionality comparable to commercial EX4. This system has several cost saving advantages associated with production, purification, storage and transportation when compared to current methods of production.

Success in using freeze-dried material will depend upon the stability of foreign proteins, ability to deliver appropriate dosage and consistency. It is crucial for freeze-dried and stored materials to preserve the integrity of the heterologous fusion protein because efficient delivery of the intact protein to the gut-associated lymphoid tissue (GALT) requires proper folding and assembly (e.g. CTB pentamers to bind GM1) (Boyhan and Daneill, 2011; Verma et al., 2010; Limaye et al., 2006). It has been shown herein that fresh and lyophilized materials form CTB pentamers and the protein profile of monomers, dimers or pentamers is identical. In the preparation of transplastomic material for oral delivery, transformed leaves must be powdered and packaged into capsules. Leaves from fully-grown plants were harvested, freeze-dried and lyophilized leaves were powdered in a grinder and stored at room temperature in moisture free containers containing silica gel. Machines are now commercially available for lyophilization and preparation of capsules with desired particle sizes.

Freeze-dried plant tissues containing vaccine antigens without CTB-fusion proteins have been stable for more than 15 months when stored at room temperature at 25° C. CTB-EX4 was stable in lyophilized tissues throughout the duration of this study. CTB-fusion proteins should be more stable because of formation of pentamers or aggregates, thereby protecting them from proteolytic degradation. While there are differences in expression levels based on leaf age or developmental stage, therapeutic protein dose should be determined in each batch of dehydrated ground powder leaves by ELISA or other quantitative methods. Although the increase in concentration of proteins expressed in plants during lyophilization is anticipated, this study reports stability, folding and functionality of therapeutic proteins bioencapsulated in plant cells. Long-term storage at room temperature, elimination of cold chain and purification steps offer the best opportunities to advance low-cost plant-derived therapeutic proteins.

Nature's Way has been marketing alfalfa capsules as nutrition supplement for several decades, illustrating the ability to eliminate pathogenic microbial threats in freeze-dried leaves. The application of freeze-drying as a source of microbial reduction was therefore investigated. Resident microbes of freshly harvested leaves were examined, and the impact of lyophilization on viable colony forming units was tested using standard microbiological assays for pathogenic bacteria, coliforms, yeast, and molds. For comparison, commercially available fresh and freeze-dried alfalfa was tested. While fresh lettuce leaves contained up to 6,000 cfu/g of microbes, lyophilized leaves expressing various foreign proteins had no detectable microbes when plated on different growth media. Therefore, the lyophilization process killed microbes present in fresh leaves. Although lyophilization is used for long-term storage of some bacteria, such freeze drying process requires lyoprotective media components including skim milk, sucrose, trehalose, fetal calf serum, BSA, etc. and would require low temperature for long-term storage (Heckly, 1985). However, in this study, no lyoprotective component was used and the lyophilized transplastomic plants were stored at room temperature up to 15 months without any harmful effect on their proteins. Moreover, the stability of the proteins expressed in transplastomic plants was unaffected even after 72 hrs of lyophilization whereas bacterial lyophilization is performed for a shorter duration. Therefore, we believe that differences in the process of lyophilization without any protective components and long duration of lyophilization should have eliminated microbes from lyophilized transplastomic plants.

For considerations on safety of oral delivery of peptides, several important questions must be considered. Multiple doses of daily use of Exenatide has been already approved by the US FDA for the treatment of type 2 diabetes (Lam and See, 2006), and CTB was also approved as adjuvant for human vaccines or as a vaccine antigen (Ryan and Calderwood, 2000; Reed et al., 2009). Because CTB is immunogenic, there could be potential concerns on fusion of these two peptides resulting in development of antibody against EX4. Two recent articles (Odumosu et al., 2011a; Odumosu et al., 2011b) investigated the mechanism of CTB fusion proteins and showed immune suppression of proteins tethered to CTB. For example, CTB-proinsulin suppressed dendritic cell (DC) activation by up-regulating Toll like receptor 2 (TLR-2). Furthermore, fusion of CTB to proinsulin was essential for enhancement of immune suppression, as co-delivery of CTB and insulin did not significantly inhibit biosynthesis of co-stimulatory factors in dendritic cells (Odumosu et al., 2011a). Likewise, another autoantigen glutamic acid decarboxylase fused with CTB strongly inhibited dendritic cell maturation through down-regulation of major co-stimulatory factors and inflammatory cytokine biosynthesis (Odumosu et al., 2011b). These results show that CTB-fusion proteins enhance immunosuppressive T lymphocytes and don't promote development of immunity of tethered proteins. Oral administration of CTB-linked autoantigens has been shown to induce tolerance by suppressing development of immune response in several allergic or autoimmune diseases (Ruhlman et al., 2007; Verma et al., 2010; Sun et al., 2010). Moreover, immunological tolerance of CTB-linked-antigen delivery in human clinical studies (phase I/phase II) has already been reported. Behcet's disease is an autoimmune eye disease caused by abnormal T cell reactivity to a specific peptide (BD peptide). In this CTB-based immunotherapy, there was no evidence for antibody production when CTB-BD peptide was orally delivered for 12~16 weeks and some patients were free of this disease up to 24 months (Stanford et al., 2004). Several studies described above show that mucosal tolerance conferred by CTB is associated with regulatory T cells that secrete immunosuppressive cytokines, transforming growth factor (TGF-β) or interleukin 10 (Sun et al., 2010; Ma and Jevnikar, 2012).

Another reason for not developing antibody is probably because these are native proteins (autoantigens) and a furin (ubiquitous protease present in all cell/tissue types) cleavage site was engineered between the CTB and the fusion protein for prompt cleavage soon after transmucosal delivery. In contrast to autoantigens, EX4 is a heterologous therapeutic peptide with 53% amino acid homology to human GLP-1.

Even though EX4 showed the anti-EX4 antibody formation during the 30-week EX4 clinical trial (Kendall et al., 2005), there are no reports of any adverse immune response from patients since it was released to the clinic in 2005, with twice or thrice daily injections. According to the latest FDA safety update for Exenatide prescribed to more than 6.6 million patients (FDA drug safety information, 2009), no adverse immune response in type II patients routinely receiving EX4 was reported. However, the Byetta (Exenatide) Summary of Product Characteristics by Eli Lilly (updated on the eMC on Jul. 5, 2012) reported antibody titres against Exenatide diminished over time and remained low through 82 weeks in most patients who developed antibodies. As discussed above, CTB conjugated autoantigens have been shown to suppress rather than stimulate the immune system, leading the immune system to tolerate the autoantigens. Therefore, it is anticipated that conjugation of EX4 to CTB should help develop tolerance rather than stimulate immune response. There are several other advantages for using CTB as a transmucosal carrier. Large mucosal area (approximately 1.8 $m^2$~2.7 $m^2$ against body weight) (Wilson, 1967) could maximize CTB binding to human intestinal epithelium (15,000 binding sites per cell) (Holmgren et al., 1975). The rapid turnover rate of cell-associated GM1 receptor on the epithelial cell (Fishman et al., 1983) is yet another advantage. However, if there is a need to investigate non-receptor mediated delivery system, protein transduction domains (PTD) are ideal due to their ability to carry cargo across the plasma membrane (Wadia and Dowdy, 2002).

The beta-TC6 cell line, a mouse pancreatic beta cell line was used for evaluation of the functionality of chloroplast derived CTB-EX4 because it exhibits the property of glucose mediated insulin secretion, triggered by binding of GLP-1 to its receptor on cell surface (Hohmeier and Newgard, 2004; Skelin et al., 2010). This in vitro study revealed that the transplastomic protein increased the insulin secretion from the pancreatic beta cell line. The insulin secretion was dose-dependent similar to the commercially available EX4.

Actual goal of this study is to deliver bioencapsulated therapeutic proteins orally with no need for any purification because purified EX4 is already available in the clinic for injectable delivery system. Therefore, animal studies were carried out to investigate the in vivo functionality of orally administered lyophilized EX4. In the animal studies, transplastomic CTB-EX4 further confirmed its ability to reduce blood glucose level similar to injections of commercial EX4 (FIG. 5). The mouse strain (C57B1/6) was chosen based on previous studies on EX4 injections (Stoffers et al., 2000). Non-obese diabetic mouse model can't be used for this study because insulin secretion is impaired in this mouse model. Other mouse models used for type 2 (spontaneous, chemically induced, surgical, transgenic/knock-out diabetic mice) are only suitable for long-term evaluation studies (Srinivasan and Ramarao, 2007). So blood glucose level of mice was intentionally spiked to mimic diabetic symptoms in order to explore the efficacy of orally delivered EX4 on hyperglycemic condition. The amount of EX4 administered orally to mouse was about 5,000 times higher than that of i.p. injections. It has been well known that EX4 lowers blood glucose levels by increasing insulin secretion from beta cell in a glucose dependent manner, contrasting other insulin secretagogues (eg, sulfonylureas) by which insulin secretion is increased regardless of glucose concentrations (Kolterman et al., 2003). So the concern about the risk of hypoglycemia can be eliminated even when excess amount of EX4 was administered, owing to the glucose dependent insulinotropic mechanism of EX4. This is one of reasons why we chose the EX4 to be expressed in an encapsulated form using chloroplasts for oral delivery. Actually, there was no detrimental effect on mice even when we delivered the 5,000 times higher dose of CTB-EX4 over i.p. injection. In a previously reported investigation (Young et al., 1999), the glycemic control potency of EX4 was tested with diabetic db/db mice in a range from 0.001 µg to 10 µg of EX4 per mouse. There was no harmful effect on mice even in higher dose injections (1 and 10 µg) in which plasma glucose was rather maintained at stably lowered level for a longer period than lower dosages (0.001, 0.01, and 0.1 µg). In addition, all of the bioencapsulated CTB-EX4 will not be delivered into the circulatory system due to a direct passage of gastrointestinal tract and degradation of non-bioencapsulated CTB-EX4 in stomach. Therefore, lyophilized and bioencapsulated CTB-EX4 system could provide a convenient and cost-effective delivery method as an alternative way to replace current injectable system for the treatment of type II diabetes, without causing a severe side effect such as hypoglycemia.

The current cost of Exenatide for daily use (twice daily) exceeding several thousand dollars annually is not available for a large population in developing countries, earning <$2/day (Bond, 2006). But producing Exenatide in the lettuce chloroplast transformation system should provide a solution to the existing problem and would significantly lower the cost of incretin treatment for type 2 diabetes. So the idea presented in this study is intriguing and potentially could benefit the lives and economy of people suffering from type 2 diabetes Experimental Procedures Related to Examples 1-6
Vector Construction, Transgene Integration, Regeneration, and Evaluation of Transplastomic Plants The CTB-EX4 chimeric gene (465 bp) was synthesized with specific primer sets. One forward primer: DV42 (5'-TTCATATGACACCTCAAAATATTACTGATT-3'; SEQ ID NO: 3) and three reverse primers: R1-EX4 (5'-CATTTGTT-TAGATAAATCAGAAGTGAAAGTACCTTCAC-CATGACGTTTACGCCGGGGCCC-3'; SEQ ID NO: 4), R2-EX4 (5'-CCGTTTTTTAACCATTCAATGAATAAAC GTACAGCTTCTTCTTCCATTTGTTTAGATAAA-3'), R3-EX4 (5'-AGTTCTAGATCAAGAAGGAGGAG-GAGCACCAGAAGAAGGACCACCGTTTTTTAAC-CATTC-3'; SEQ ID NO: 6) were used. The three reverse primers had overlapping sequence for each other to elongate the coding sequence. The PCR amplified and sequence-confirmed fragment was cloned into the chloroplast transformation vector, pLD. Delivery of chloroplast vector, regeneration, evaluation, and quantification of transplastomic lines were done according to the previously published methods (Verma et al., 2008) Immunoblot analyses were carried out with rabbit anti-CTB polyclonal antibody (GeneWay), rabbit anti-EX4 polyclonal antibody (Abcam), and anti-PA polyclonal antibody (Ruhlman et al., 2010). The binding assay of functional pentameric form of CTB-EX4 to GM1 ganglioside receptor was carried out as described previously (Limaye et al., 2006).

Lyophilization

Crumbled and frozen samples were transported to the lyophilizer on liquid nitrogen and treated for varying durations of 24, 48 and 72 hrs. Optimization based on percentage of dehydration was measured through relative gravimetric analysis. Lyophilization was carried out with the aid of VirTis BenchTop 6K freeze dryer system in vacuum at −52° C. at 0.036 mBar. The lyophilized leaf materials were ground in a coffee grinder (Hamilton Beach) at maximum speed for 2 min (pulse on 10 sec and off 30 sec) and sieved using mesh (Sigma, size: 100). After that, fine powder was stored in capsules under moisture-free condition at room temperature with silica gel.

Evaluation of Microbes

Fresh and lyophilized materials were ground under aseptic conditions, mixed with peptone-saline diluents for serial dilutions to obtain colony count. Nutrient Broth Agar or Luria-Bertani Broth Agar were used for microbial growth for 48-72 hr at 37° C. Colony forming unit (CFU) was obtained with means and standard deviations from two repeats of independent experiments.

Purification of CTB-EX4, Furin Cleavage and Silver Staining

To purify CTB-EX4 fusion proteins, pierce crosslink IP kit (Thermo Scientific) was used according to the manufacturer's protocol. The eluted fractions were dialyzed against PBS 3 times, aliquoted and stored at −20° C. Furin cleavage assay was performed as previously described (Munck et al., 1999). Released CTB fragments and EX4 peptides were detected via immunoblot using anti-CTB polyclonal antibody and silver stain (Boyhan and Daniell, 2011), respectively after resolution in Tricine-SDS-PAGE gel (Schägger, 2006).

In Vitro Cell Culture Assay

The mouse pancreatic cell line, beta-TC6 was cultured in DMEM (ATCC) medium supplemented with 15% heat inactivated fetal bovine serum, 100 U/ml penicillin and 100 U/ml streptomycin at 37° C. under 5% $CO_2$ condition. The beta-TC6 cells were harvested at 70-80% confluence and incubated in glucose-free Krebs-Ringer bicarbonate buffer for 1 hr at 37° C. The buffer was then removed and cells were incubated in Krebs-Ringer bicarbonate buffer with the various concentrations of purified CTB-EX4, commercial EX4 (California Peptide Research) and glucose (10 mM) for 45 min at 37° C. PBS was used as the negative control. The amount of insulin secreted into the supernatant was determined using the mouse insulin ELISA kit (Crystal Chem).

Animal Study for Evaluation of Lowering Effect of CTB-EX4

Ten-week-old female mice (C57BL/6) were purchased from The Jackson Laboratory. Mice were housed in UCF animal facility under controlled humidity and temperature conditions. All animal studies were performed according to ethical standards and protocols approved by the UCF Institutional Animal Care Use Committee (IACUC). The fine powder of the lyophilized leaf material expressing CTB-EX4 was resuspended in a ratio of 100 mg to 800 µl of sterilized PBS. Then 300 ul out of 900 ul of resuspended solution was given to each mouse ($1.2 \times 10^{-2}$ µmol of EX4-CTB/mouse, 15 weeks old). Commercial EX4 was resuspended in PBS and sterilized using 0.2 µm syringe filter. Mice were given 200 ul of PBS containing EX4 (0.01 µg, $2.39 \times 10^{-6}$ µmole of EX4/mouse) and PBS only as control. For glucose spike in mice, glucose (2 g/kg) was administered intraperitoneally. Blood was collected from tail vein at 30, 90, 120, 150, and 180 min after or 30 min before oral gavage or i.p. injection of commercial EX4. Glucose levels were measured using Accu-Chek (Roche).

Statistics

Single factor ANOVA was used for statistical evaluation of data. Differences with $P<0.05$ were considered significant. Data are presented as the mean±SD.

REFERENCES

Arlen, P., Falconer, R., Cherukumilli, S., Cole, A., Cole, A. M., Oishi, K. K. and Daniell, H. (2007) Field production and functional evaluation of chloroplast-derived interferon-alpha2b. *Plant Biotechnol. J.* 5, 511-525.

Arntzen, C. J. (2008) Using tobacco to treat cancer. *Science,* 321, 1052-1053.

Baggio, L. L. and Drucker, D. J. (2007) Biology of incretins: GLP-1 and GIP. *Gastroenterology,* 132, 2131-2157.

Baggio, L. L., Huang, Q., Brown, T. J. and Drucker, D. J. (2004) A recombinant human glucagon-like peptide (GLP)-1-albumin protein (Albugon) mimics peptidergic activation of GLP-1 receptor-dependent pathways coupled with satiety, gastrointestinal motility, and glucose homeostasis. *Diabetes,* 53, 2492-2500.

Barnhart, K. F., Christianson, D. R., Hanley, P. W., Driessen, W. H., Bernacky, B. J., Baze, W. B., Wen, S., Tian. M., Ma, J., Kolonin, M. G., Saha, P. K., Do, K. A., Hulvat, J. F., Gelovani, J. G., Chan, L., Arap, W. and Pasqualini, R. (2011) A peptidomimetic targeting white fat causes weight loss and improved insulin resistance in obese monkeys. *Sci. Transl. Med.* 3, 108ra112.

Bellmann-Sickert, K. and Beck-Sickinger, A. G. (2010) Peptide drugs to target G protein-coupled receptors. *Trends Pharmacol. Sci.* 31, 434-441.

Bond, A. (2006) Exenatide (Byetta) as a novel treatment option for type 2 diabetes mellitus. *Pro (Bayl Univ Med cent).* 19, 281-284.

Boyhan, D. and Daniell, H. (2011) Low-cost production of proinsulin in tobacco and lettuce chloroplasts for injectable or oral delivery of functional insulin and C-peptide. *Plant Biotechnol. J.* 9, 585-598.

Centers for Disease Control and Prevention. National diabetes fact sheet: national estimates and general information on diabetes and prediabetes in the United States, 2011. Atlanta, Ga.: U.S. Department of Health and Human Services, Centers for Disease Control and Prevention, 2011.

Chia, C. W. and Egan, J. M. (2005) Biology and therapeutic potential of GLP-1 in the treatment of diabetes. *Drug Discov. Today Dis. Mech.* 2, 295-301.

Daniell, H. (2007) Transgene containment by maternal inheritance: Effective or elusive? *Proc. Natl. Acad. Sci. USA,* 104, 6879-6880.

Daniell, H., Ruiz, G., Denes, B., Sandberg, L. and Langridge, W. (2009b) Optimization of codon composition and regulatory elements for expression of human insulin like growth factor-1 in transgenic chloroplasts and evaluation of structural identity and function. *BMC Biotechnol.* 9, 33.

Daniell, H., Singh, N. D., Mason, H. and Streatfield, S. J. (2009a) Plant-made vaccine antigens and biopharmaceuticals. *Trends Plant Sci.* 14, 669-679.

Davidson, J. A. (2009) Advances in therapy for type 2 diabetes: GLP-1 receptor agonists and DPP-4 inhibitors. *Cleve Clin. J. Med.* 76, S28-S38.

Davoodi-Semiromi, A., Schreiber, M., Nalapalli, S., Verma, D., Singh, N. D., Banks, R. K., Chakrabarti, D. and Daniell, H. (2010) Chloroplast-derived vaccine antigens confer dual immunity against cholera and malaria by oral or injectable delivery. *Plant Biotechnol. J.* 8, 223-242.

Doyle, M. E., Theodorakis, M. J., Holloway, H. W., Bernier, M., Greig, N. H. and Egan, J. M. (2003) The importance of the nine-amino acid C-terminal sequence of exendin-4 for binding to the GLP-1 receptor and for biological activity. *Regul. Pept.* 114, 153-158.

Fernández-San Millán, A., Ortigosa, S. M., Hervás-Stubbs, S., Corral-Martínez, P., Seguí-Simarro, J. M., Gaétan, J., Coursaget, P. and Veramendi, J. (2008) Human papillomavirus L1 protein expressed in tobacco chloroplasts self-assembles into virus-like particles that are highly immunogenic. *Plant Biotechnol. J.* 6, 427-441.

Fishman, P. H., Bradley, R. M., Hom, B. E. and Moss, J. (1983) Uptake and metabolism of exogenous gangliosides by cultured cells: effect of choleragen on the turnover of GM1. *J. Lipid Res.* 24, 1002-1011.

Gisby, M. F., Mellors, P., Madesis, P., Ellin, M., Laverty, H., O'Kane, S., Ferguson, M. W. and Day, A. (2011) A synthetic gene increases TGFβ3 accumulation by 75-fold in tobacco chloroplasts enabling rapid purification and folding into a biologically active molecule. *Plant Biotechnol. J.* 9, 618-628.

Hamman, J. H. and Steenekamp, J. H. (2011) Oral peptide drug delivery: strategies to overcome challenges. In *Peptide Drug Discovery and Development: Translational Research in Academia and Industry* (Castanho, M. and Santos, N., eds), pp. 71-90. Weinheim:WILEY-VCH.

Heckly, R. J. (1985) Principles of preserving bacteria by freeze-drying. *Develp. Ind. Microbiol.* 26, 379-395.

Hohmeier, H. E. and Newgard, C. B. (2004) Cell lines derived from pancreatic islets. *Mol. Cell Endocrinol.* 228, 121-128.

Holmgren, J., Lönnroth, I., Månsson, J. and Svennerholm, L. (1975) Interaction of cholera toxin and membrane GM1 ganglioside of small intestine. *Proc. Natl. Acad. Sci. USA,* 72, 2520-2524.

Hupe-Sodmann, K., McGregor, G. P., Bridenbaugh, R., Göke, R., Göke, B., Thole, H., Zimmermann, B. and Voigt, K. (1995) Characterisation of the processing by human neutral endopeptidase 24.11 of GLP-1(7-36) amide and comparison of the substrate specificity of the enzyme for other glucagon-like peptides. *Regul. Pept.* 22, 149-156.

Kendall, D. M., Riddle, M. C., Rosenstock, J., Zhuang, D., Kim, D. D., Fineman, M. S., Baron, A. D. (2005) Effects of exenatide (exendin-4) on glycemic control over 30 weeks in patients with type 2 diabetes treated with metformin and a sulfonylurea. *Diabetes Care* 28, 1083-1091.

Kieffer, T., McIntosh, C. and Pederson, R. (1995) Degradation of glucose-dependent insulinotropic polypeptide and truncated glucagon-like peptide 1 in vitro and in vivo by dipeptidyl peptidase IV. *Endocrinology,* 136, 3585-3596.

Kolterman, O. G., Buse, J. B., Fineman, M. S., Gaines, E., Heintz, S., Bicsak, T. A., Taylor, K., Kim, D., Aisporna, M., Wang, Y. and Baron, A. D. (2003) Synthetic exendin-4 (exenatide) significantly reduces postprandial and fasting plasma glucose in subjects with type2 diabetes. *J. Clin. Endocrinol. Metab.* 88, 3082-3089.

Koya, V., Moayeri, M., Leppla, S. H. and Daniell, H. (2005) Plant-based vaccine: Mice immunized with chloroplast-derived anthrax protective antigen survive anthrax lethal toxin challenge. *Infect. Immun.* 73, 8266-8274.

Lam, S. and See, S. (2006) Exenatide: A novel incretin mimetic agent for treating type 2 diabetes mellitus. *Cardiol. Rev.* 14, 205-211.

Lee, S. B., Li, B., Jin, S. and Daniell, H. (2011) Expression and characterization of antimicrobial peptides Retrocyclin-101 and Protegrin-1 in chloroplasts to control viral and bacterial infections. *Plant Biotechnol. J.* 9, 100-115.

Limaye, A., Koya, V., Samsam, M. and Daniell, H. (2006) Receptor-mediated oral delivery of a bioencapsulated green fluorescent protein expressed in transgenic chloroplasts into the mouse circulatory system. *FASEB J.* 20, 959-961.

Lovshin, J. A. and Drucker, D. J. (2009) Incretin-based therapies for type 2 diabetes mellitus. *Nat. Rev. Endocrinol.* 5, 262-269.

Ma, S. and Jevnikar, A. M. (2012) Induction of oral tolerance to treat autoimmune and allergic diseases by using transgenic plants. In: *Molecular Farming in Plants: Recent Advances and Future Prospects* (Wang, A. and Ma, S., eds), pp. 21-35. New York: Springer.

Masur, K., Tibaduiza, E. C., Chen, C., Ligon, B. and Beinborn, M. (2005) Basal receptor activation by locally produced glucagon-like peptide-1 contributes to maintaining beta-cell function. *Mol. Endorinol.* 19, 1373-1382.

McGregor, D. P. (2008) Discovering and improving novel peptide therapeutics. *Curr. Opin. Pharmacol.* 8, 616-619.

Munck, P. C., Nielsen, M. S., Jacobsen, C., Tauris, J., Jacobsen, L., Gliemann. J., Moestrup, S. K. and Madsen, P. (1999) Propeptide cleavage conditions sortilin/neurotensin receptor-3 for ligand binding. *EMBO J.* 18, 595-604.

Odumosu, 0., Nicholas, D., Payne, K. and Langridge, W. (2011b) Cholera toxin B subunit linked to glutamic acid decarboxylase suppresses dendritic cell maturation and function. *Vaccine,* 29, 8451-8458.

Odumosu, 0., Payne, K., Baez, I., Jutzy, J., Wall. N. and Langridge, W. (2011a) Suppression of dendritic cell activation by diabetes autoantigens linked to the cholera toxin B subunit. *Immunobiology,* 216, 447-456.

Reed, S. G., Bertholet, S. Coler, R. N. and Friede, M. (2009) New horizons in adjuvants for vaccine development. *Trends Immunol.* 30, 23-32.

Riddle, M. C., Henry, R. R., Poon, T. H., Zhang, B., Mac, S. M., Holcombe, J. H., Kim, D. D. and Maggs, D. G. (2006) Exenatide elicits sustained glycaemic control and progressive reduction of body weight in patients with type 2 diabetes inadequately controlled by sulphonylureas with or without metformin. *Diabetes Metab. Res. Rev.* 22, 483-491.

Ryan, E. T. and Calderwood, S. B. (2000) Cholera vaccines. *Clin. Infect. Dis.* 31:561-565.

Ruhlman, T., Ahangari, R., Devine, A., Samsam, M. and Daniell, H. (2007) Expression of cholera toxin B-proinsulin fusion protein in lettuce and tobacco chloroplasts-oral administration protects against development of insulitis in non-obese diabetic mice. *Plant Biotechnol. J.* 5, 495-510.

Ruhlman, T., Verma, D., Samson, N. and Daniell, H. (2010) The role of heterologous chloroplast sequence elements in transgene integration and expression. *Plant Physiol.* 152, 2088-2104.

Sánchez, J. and Holmgren, J. (2008) Cholera toxin structure, gene regulation and pathophysiological and immunological aspects. *Cell Mol. Life Sci.* 65, 1347-1360.

Schägger, H. (2006) Tricine-SDS-PAGE. *Nat. Protoc.* 1, 16-22.

Skelin, M., Rupnik, M. and Cencic, A. (2010) Pancreatic beta cell lines and their applications in diabetes mellitus research. *Altex,* 27, 105-113.

Scheen, A. J. (2003) Pathophysiology of type 2 diabetes. *Acta Clin. Belg.* 58, 335-341.

Srinivasan, K. and Ramarao, P. (2007) Animal models in type 2 diabetes research: an overview. *Indian J. Med. Res.* 125, 451-472.

Sun, J. B. Czerkinsky, C. and Holmgren, J. (2010) Mucosally induced immunological tolerance, regulatory T Cells and the adjuvant effect by cholera toxin B subunit. *Scand. J. Immunol.* 71, 1-11.

Stanford, M., Whittall, T., Bergmeier, L. A., Lindblad, M., Lundin, S., Shinnick, T., Mizushima, Y., Holmgren, J. and Lehner, T. (2004) Oral tolerization with peptide 336-351 linked to cholera toxin B subunit in preventing relapses of uveitis in Behcet's disease. *Clin. Exp. Immunol.* 137, 201-208.

Stoffers, D. A., Kieffer, T. J., Hussain, M. A., Drucker, D. J., Bonner-Weir, S., Habener, J. F. and Egan, J. M. (2000) Insulinotropic glucagon-like peptide 1 agonists stimulate expression of homeodomain protein IDX-1 and increase islet size in mouse pancreas. *Diabetes,* 49, 741-748.

Verma, D., Moghimi, B., LoDuca, P. A., Singh, H. D., Hoffman, B. E., Herzog, R. W. and Daniell, H. (2010) Oral delivery of bioencapsulated coagulation factor IX prevents inhibitor formation and fatal anaphylaxis in hemophilia B mice. *Proc. Natl. Acad. Sci. USA,* 107, 7101-7106.

Verma, D., Samson, N. P., Koya, V. and Daniell, H. (2008) A protocol for expression of foreign genes in chloroplasts. *Nat. Protoc.* 3, 739-758.

Wadia, J. S. and Dowdy, S. F. (2002) Protein transduction technology. *Curr. Opin. Biotechnol.* 13, 52-56.

Wild, S., Roglic, G., Green, A., Sicree, R. and King, H. (2004) Global prevalence of diabetes. *Diabetes Care,* 27, 1047-1053.

Wilson, J. P. (1967) Surface area of the small intestine in man. *Gut,* 8, 618-621.

Young, A. A., Gedulin, B. R., Bhaysar, S., Bodkin, N., Jodka, C., Hansen, B. and Denaro, M. (1999) Glucose-lowering and insulin-sensitizing actions of exendin-4: studies in obese diabetic (ob/ob, db/db) mice, diabetic fatty Zucker rats, and diabetic rhesus monkeys (Macaca mulatta). *Diabetes,* 48, 1026-1034.

Yusibov, V., Streatfiled, S. J. and Kushnir, N. (2011) Clinical development of plant-produced recombinant pharmaceuticals: vaccines, antibodies and beyound. *Hum. Vaccin.* 7, 313-321.

The invention claimed is:

1. A plant plastid comprising a plastid genome transformed with a heterologous expression cassette consisting of, as operably linked components in the 5' to the 3' direction of translation, a flanking sequence having homology to a trnI region in the plastid genome, a Prrn promoter operative in said plastid, an aadA selectable marker sequence or an antibiotic free selectable marker sequence, a psbA 5' untranslated region sequence, a cholera toxin B subunit (CTB)-Exendin fusion gene sequence, a psbA 3' untranslated region sequence, and a flanking sequence having homology to a trnA region in the plastid genome, said expression cassette being integrated into said plastid genome such that said CTB-Exendin is expressed in and present in said plastid, wherein the CTB-Exendin 4 fusion protein has a hinge region, and a furin cleavage site between the CTB and the Exendin 4, and wherein the hinge-furin cleavage site-exendin portion consists of SEQ ID NO: 7, said plastid being suitable for oral administration of said CTB-Exendin 4 to a subject in need thereof.

2. An edible plant cell comprising the plastid of claim 1.

3. A lettuce, apple, tomato or carrot plant comprising the plant cell of claim 2.

4. A method of retarding the development of or treating Type II diabetes in a subject in need thereof, said method comprising orally administering to said subject a composition comprising plastid transformed plant cells of claim 2, said composition comprising a plant remnant.

5. The method of claim 4, wherein said plant remnant comprises rubisco.

6. The plant cell of claim 2, wherein said plant cell is homoplasmic and comprises an antibiotic free selectable marker.

7. Transplastomic progeny or seeds of the plant of claim 3, said progeny or seeds having a plastid genome transformed with said CTB-exendin 4 expression cassette.

8. The plant of claim 3, wherein said plant is homoplasmic and stably transformed.

9. A process for producing a CTB-Exendin 4 polypeptide, said process comprising:
a) generating the lettuce plant of claim 3, which is *Lactuca sativa*;
b) growing said stably transformed *Lactuca sativa* plant under conditions suitable for expression and production of said CTB-Exendin polypeptide; and
c) optionally homogenizing material of said stably transformed *Lactuca sativa* plant to produce homogenized material.

10. The method of claim 9, further comprising purifying CTB-Exendin 4 from said homogenized material.

11. The method of claim 9, wherein said homogenized material is dried to produce a powder.

12. The method of claim 11, further comprising encapsulating said powder.

13. The plant cell of claim 2, which is freeze dried and retains therapeutic effectiveness when stored at room temperature for at least 2, 3, 4, 6, 7, 8, 9, 10, 11, 12, 13, 14, 15, 16, 17, 18, 19, 20, or 21 weeks.

14. The method of claim 4, wherein said subject in need exhibits at least one symptom comprising ketoacidosis, Kussmaul breathing, nausea, vomiting, abdominal pain, polyuria, polydipsia, polyphagia, increased or decreased insulin levels, and elevated serum glucose.

15. The method of claim 4, wherein said patient in need exhibits impaired glucose tolerance.

16. The method of claim 4, wherein said patient in need exhibits fasting glucose levels from 100 to 125 mg/dL (5.6 to 6.9 mmol/L).

17. The method of claim 4, wherein said patient in need exhibits plasma glucose at or above 140 mg/dL (7.8 mmol/L), but not over 200 mg/dL (11.1 mmol/L), two hours after a 75 g oral glucose load.

* * * * *